US006475730B1

(12) United States Patent
Douglas et al.

(10) Patent No.: US 6,475,730 B1
(45) Date of Patent: Nov. 5, 2002

(54) DETECTING NUCLEIC ACIDS

(75) Inventors: Kenneth T Douglas, Littleborough; Elena V Bichenkova, Manchester, both of (GB)

(73) Assignee: The Victoria University of Manchester, Manchester (GB)

( * ) Notice: Subject to any disclaimer, the term of this patent is extended or adjusted under 35 U.S.C. 154(b) by 0 days.

(21) Appl. No.: 09/467,015

(22) Filed: Dec. 20, 1999

(30) Foreign Application Priority Data

Dec. 19, 1998 (GB) ............................................. 9827912

(51) Int. Cl.[7] ........................... C12Q 1/68; C12P 19/34; C07H 19/00; C07H 21/02
(52) U.S. Cl. ......................... 435/6; 435/91.2; 536/22.1; 536/25.3; 548/100; 548/120; 548/146; 548/148; 548/181; 548/215
(58) Field of Search .................... 435/6, 91.2; 536/22.1, 536/25.3; 548/100, 120, 146, 148, 181, 215, 217, 223

(56) References Cited

U.S. PATENT DOCUMENTS

| | | | |
|---|---|---|---|
| 5,466,578 A | 11/1995 | Kidwell | 435/6 |
| 6,045,995 A | * 4/2000 | Cummins et al. | 435/6 |
| 6,140,048 A | * 10/2000 | Muller et al. | 435/6 |

FOREIGN PATENT DOCUMENTS

EP 0 318 245 5/1989
EP 0 810 291 12/1997

OTHER PUBLICATIONS

Benson et al., "Exciplex Fluorescence in Inclusio Complexes of Napthalene derivatives", *Tetrahedron Letters*, vol. 37 (28), pp. 4833–4836, Apr. 1996.*
Paris et al., "Probing DNA sequences in solution with a monomer–excimer fluorescence color change", *Nucleic Acids Research*, vol. 26 (16), pp. 3789–3793, Jun. 1998.*
Verhoeven et al., "Solvent effects on the structure of fluorescent "exciplexes" in rigidly–, flexibly–, and non–bridged donor–acceptor systems", *Pure & Applied Chemistry*, vol. 65 (8), pp. 1717–1722, Aug. 1993.*
Cao et al., "Effects of High Magnetic Field on the Intramolecular Exciplex Fluorescence of Chain–linked Phenanthrene and Dimethylaniline", *Journal of Physical Chemistry*, vol. 101, pp. 407–411, Jan. 1997.*
Bichenkova et alk, "Structual Studies by High–Field NMR Spectroscopy of a Binary–Addressed Complementary Oligonucleotide System Juxataposing Pyrene and Perfluoro–Azide Units", Journal of Biomolecular Structure & Dynamics 15(2):307–320 (1997).
Ebata et al, "Nucleic Acid Hybridization Accompanied With Excimer Formation From Two Pyrene–Labeled Probes", Photochemistry and Photobiology 62(5):836–839 (1995).

* cited by examiner

Primary Examiner—W. Gary Jones
Assistant Examiner—Arun Chakrabarti
(74) Attorney, Agent, or Firm—Nixon & Vanderhye P.C.

(57) ABSTRACT

The present invention relates to a method of detecting nucleic acids and particularly to a method of analyzing for the presence and/or amount of a nucleic acid.

47 Claims, 10 Drawing Sheets

Figure 1:
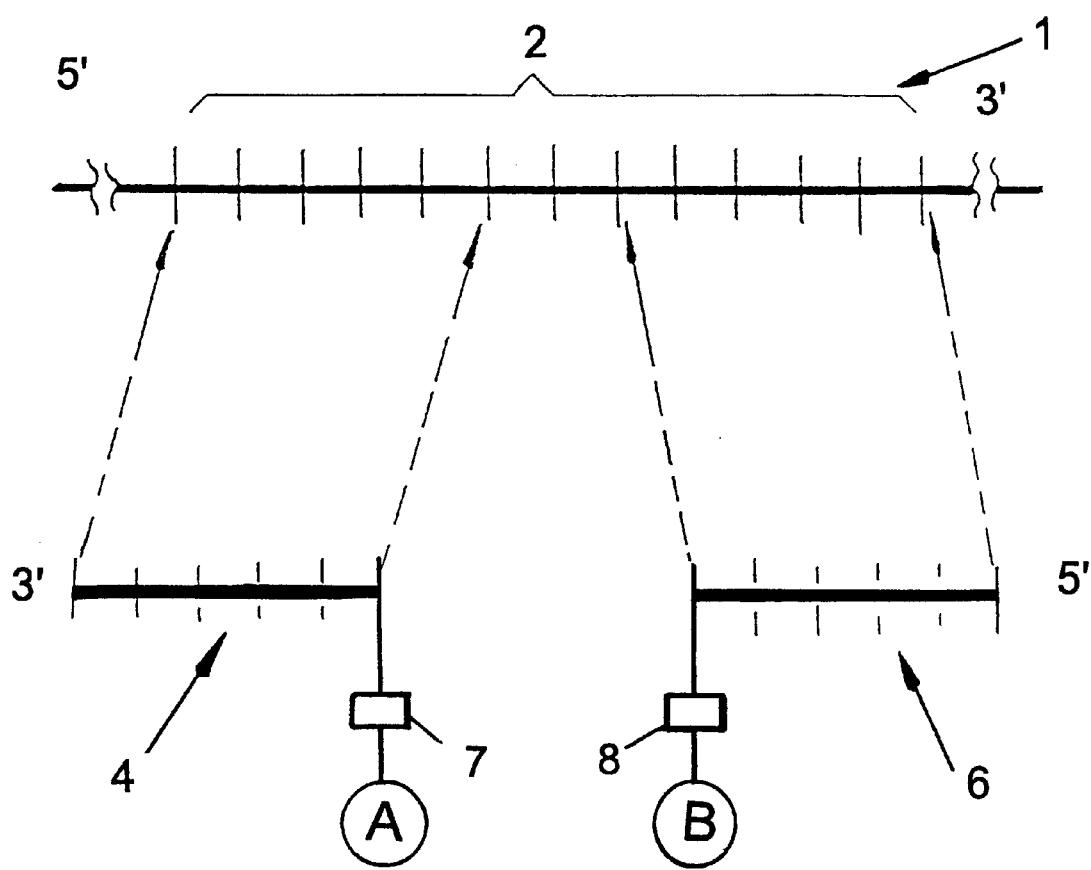

A. Continuous Alignment of oligonucleotide ON1 and ON2

(a) perfect binding without mismatches   (b) non-perfect binding with a single mis-match for ON1

B. Non-Continuous Alignment of ON1-R1 and ON2-R2 with a single gap (a) perfect binding without mis-matches   (b) non-perfect binding with a single mis-match for ON1

FIG. 10(a)
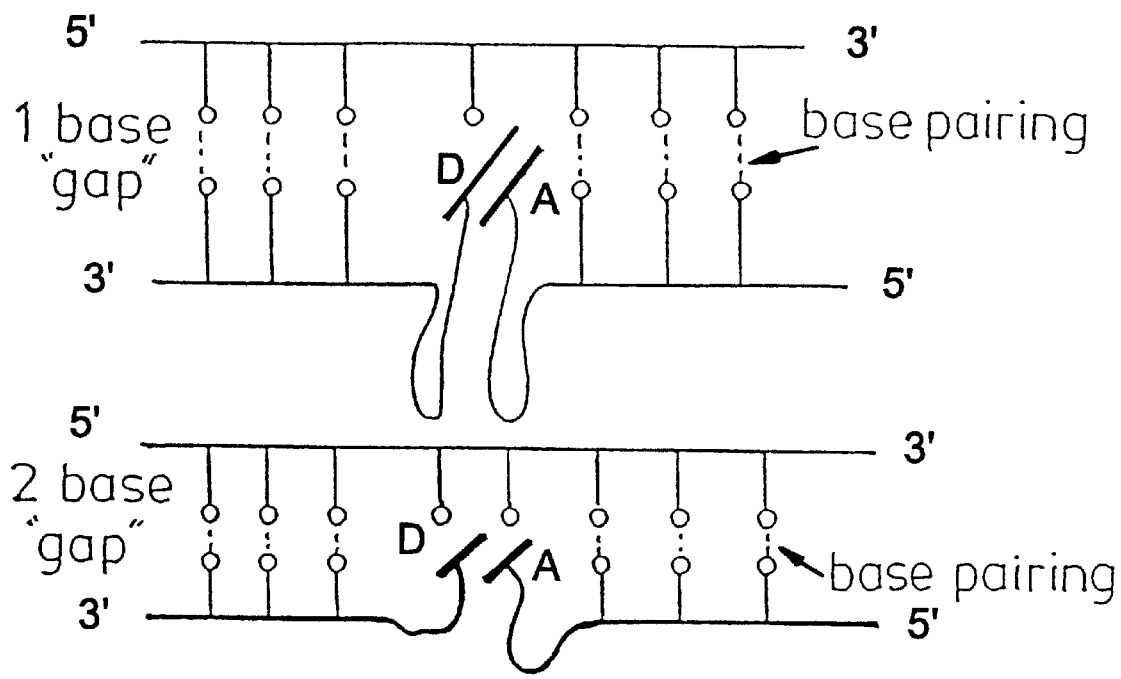
FIG. 10(b)
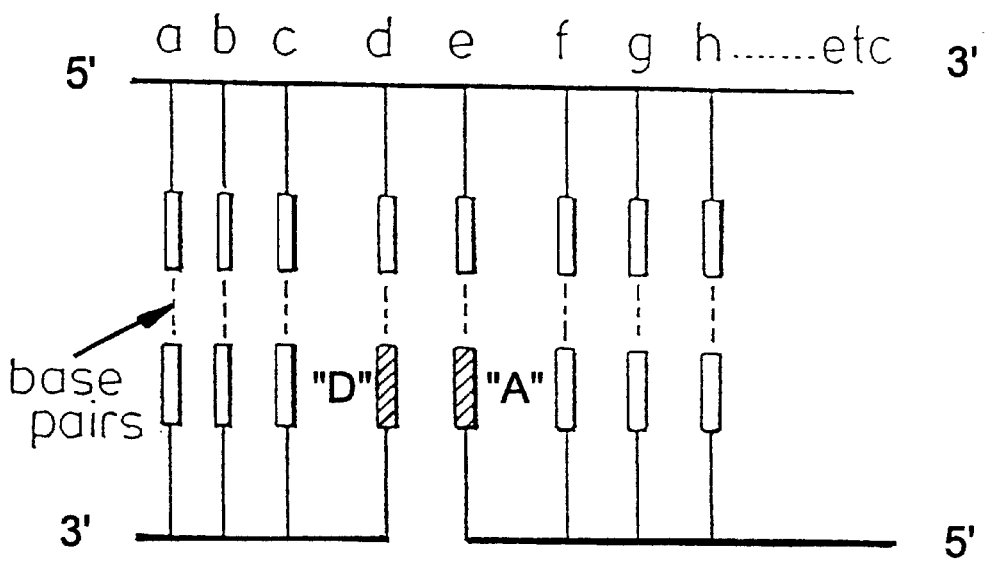
FIG. 10(c)

FIG. 11(a)
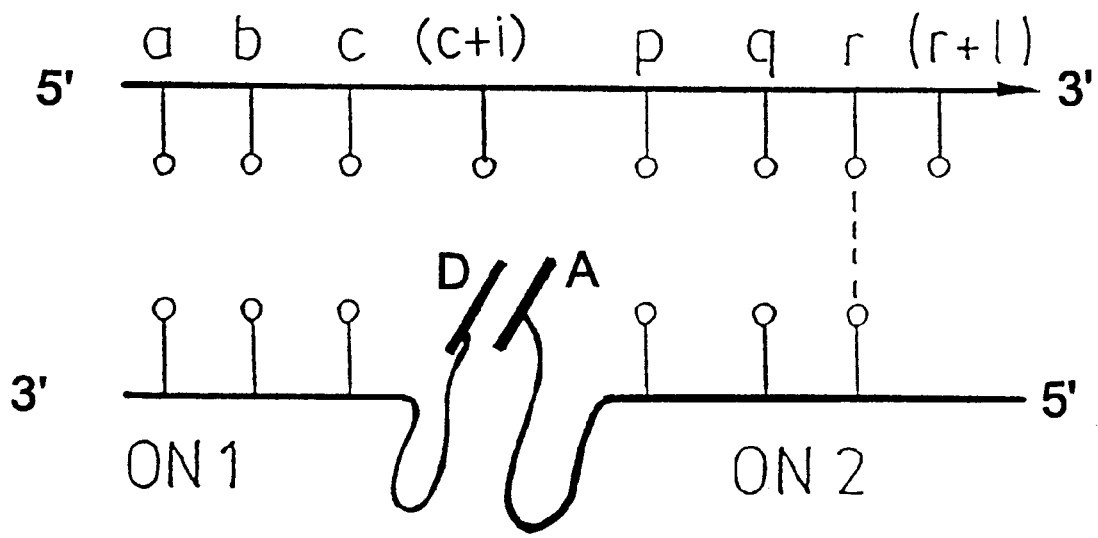
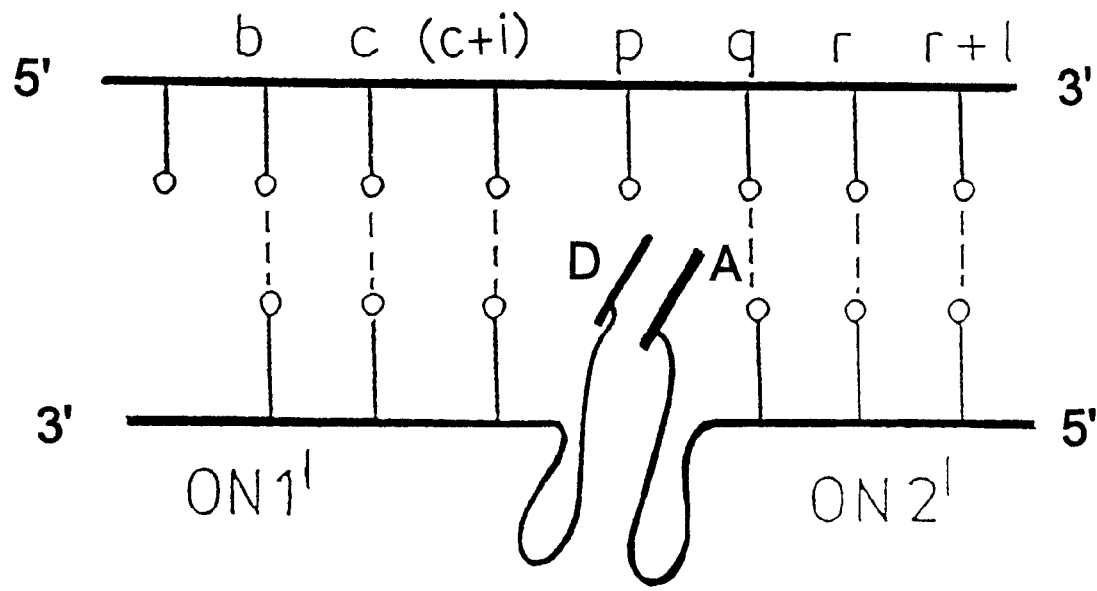
FIG. 11(b)

DETECTING NUCLEIC ACIDS

The present invention relates to a method of detecting nucleic acids and particularly to a method of analysing for the presence and/or amount of a nucleic acid.

There are many known methods of detecting nucleic acids.

For example, in the case of analysing for the presence of a particular nucleic acid in a sample containing only a very small amount of the acid it is known to use the Polymerase Chain Reaction (PCR) to amplify the amount of the acid which may then be detected, e.g. by using a labelled oligonucleotide probe. It is however known that the PCR reaction has the disadvantage that it can give rise to artefacts resulting in "false positives". Furthermore, PCR is difficult to apply in situ in cells and is time consuming as excess of probing reagents have to be removed.

A further technique for analysis of nucleic acids is Fluorescence Resonance Energy Transfer (FRET). Two oligonucleotide probes are used in this method, one being associated with a photosensitiser (A) and the other with a photoemitter (B). In a FRET assay, the probes are such that when hybridized to a target nucleic acid strand to be detected the distance between the photosensitiser (A) and the photoemitter (B) is 5–10 nm in any dimension. To perform the assay, photosensitiser (A) is excited with electromagnetic radiation of the appropriate wavelength. If the two probes have hybridized to the nucleic acid strand adjacent to each other then photosensitiser (A) is able to excite photoemitter (B) by resonance energy transfer. Radiation emitted by (B) (which is of different wavelength from the exciting radiation) may then be detected to confirm presence of the target strand. The FRET technique does however have the disadvantage that because the resonance energy transfer occurs over a distance of 5–10 nm (equivalent to a distance of 4 bp) it is possible for the FRET signal to arise between non-specifically hybridized probes or between probes and an interacting nucleic acid chain. If the FRET partners are also not optimally aligned the efficiency of energy transfer can be low thus limiting the magnitude of the detectable signal.

A further proposal for the assay of nucleic acids is disclosed in U.S. Pat. No. 5,332,659 (Kidwell). This technique relies on establishing a sufficiently high, localised concentration of excimer-forming components to result in formation of an excimer which may be detected to assay the nucleic acid. In the preferred embodiment of this technique a sensing nucleic acid strand is labelled with a plurality of the excimer forming components (e.g. pyrene) attached to the nucleic acid chain by flexible linkers whereby said components are able to move randomly relative to each other and interact to participate in excimer formation.

To perform the assay, a sample potentially containing the target nucleic acid is probed with the sensing strand whilst the system is irradiated (e.g. by a laser) with electromagnetic radiation capable of effecting formation of an excimer if two excimer-forming components are within sufficiently close proximity. In the non-hybridized sensing strand, there is a relatively high probability of excimer formation resulting from random movement of the excimer forming components. However when the sensing strand is hybridized to the target, the former (i.e. the sensing strand) adopts a configuration in which interaction of the excimer-forming components is considerably less likely so that there is a reduced signal compared to a control in which no target is present.

This proposal has the disadvantage of relying on a decrease in signal which may be difficult to detect and of achieving excimer formation by random movement (allowed by virtue of the linkers) of the component parts thereof. Further a decrease in signal would also result from non-specific hybridisation of probe DNA with other structurally similar regions.

In an alternative embodiment disclosed in U.S. Pat. No. 5,332,659, it is proposed that the sensing strand be more heavily labelled. In this embodiment, the length of the linker is selected to reduce the freedom of movement of the excimer-forming components thus minimising (but not eliminating) their interaction in solution. The sensing strand is capable of binding to the target strand such that the sensing strand undergoes structural rearrangement to bring the excimer-forming components sufficiently close to each other for excimer formation. However once again the formation of the excimer relies on a sufficiently high effective concentration of the excimer-forming components being provided, and being able to interact, by the presence of the linkers.

It is acknowledged in U.S. Pat. No. 5,332,659 that all of the disclosed embodiments relating to detection of polynucleic acids result in some complex formation whether the target polynucleic acid strand is present or absent. This could give rise to a false reading.

A similar technique is disclosed in U.S. Pat. No. 5,466,578 (which is Continuation-in-Part of U.S. Pat. No. 5,332,659) but with the modification of using a quaternary ammonium surfactant to enhance light or emission or absorbance. However the same disadvantages as discussed for U.S. Pat. No. 5,332,659 still apply.

EP-A-0 810 291 discloses a method for detection of nucleic acid (NA) sequences using hybridisation of nonradioactive probes with target NA sequences. The method is based on the hybridization of the target NA molecule with two (or more) oligonucleotides, ON1 and ON2, bearing chromophoric labelling groups at their 5'-terminus and 3'-terminus, respectively, and being complementary to the neighbouring base-pairing sites of the target NA. Thus, under hybridizing conditions, the two oligonucleotides are capable of hybridizing to the target sequence (if present) such that the 5' terminal nucleotide of the first probe and the 3' terminal nucleotide of the second probe are hybridized to adjacent bases of the target sequence.

The 5' individual chromophoric labelling groups R1 and R2 are each capable of forming with the other chromophoric group a complex which fluoresces at a longer wavelength than either of the individual chromophoric groups. The complex is only formed on photo-irradiation if the two chromophoric groups are brought into complex forming relationship and this only occurs if both oligonucleotides probes are hybridized to the target sequence. Thus by monitoring for fluorescence at the emission wavelength for the complex it is possible to determine whether or not the particular polynucleotide target is present (since fluorescence of the emission wavelength of the complex will only be observed of the two probes are hybridized to the target).

To ensure that the complex can be formed, it is stated in EP-A-0 810 291 that intercalation of the chromophoric groups into the double stranded nucleic acid formed by hybridisation of the probes must be avoided.

It is possible in the technique of EP-A-0 810 291 to employ a plurality of pairs of probes as described each of which, if hybridized to the appropriate target sequence, will result in production of a complex having a different fluorescence emission so that by detecting for these different wavelengths the analysis procedure is capable of detecting a plurality of different target sequences.

The preferred complex for use in the technique of EP-A-0 810 291 is a excimer (i.e. a fluorescent complex)

formed when two identical complex forming partners (e.g. pyrene) are brought into the correct positional relationship to each other and photo-irradiated and the invention is exemplified by excimers. Similar subject matter to EP-A-0 810 291 is disclosed in Ebata et al. Photochem. Photobiol. (1995) v 62, pp836–839 and Ebata et al. Nucl Acids Symp (1995) Series No 34, pp187–188) and in P. L. Paris et al. Nucl. Acids Res.1 (1998), v26, pp 3789–373.

There is also a reference in EP-A-0 810 291 to the possibility of the complex being an exciplex but no specific details with regard to such a complex are given. An exciplex is a heterocomplex analogue of an excimer and is formed, on photo-irradiation, when appropriate donor and acceptor species (e.g. pyrene and dimethyl analine) come into the required positional relationship relative to each other, the exciplex complex then dissociating with emission of fluorescence which is detectably different from that of either of the exciplex forming partners.

Exciplexes have the characteristics that it is possible by altering the electron affinity and ionisation potential of the contributing partners to "tune" the emission wavelength of the complex including the wavelength and temporal characteristics, as may be used in time-resolved fluorescence. For example, an exciplex formed from N,N-diethylamine with chrysene emits at ca 420 nm but one formed with N,N-diethylamine with perylene emits at ca 520 nm.

More particularly, the emission characteristics can be tuned in a predictable sense by the fine chemical structures of the partners, for example the emitted light frequency being linearly related to the difference in electron donor/electron acceptor strengths of the partners (see for example D. RehM, S. Naturforsch (1970) Vol 25a 1442–1447; J. B. Birks "Photophysics of Aromatic Molecules" published by Wiley Interscience, London.

The procedure of EP-A-0 810 291 (and the related prior art) suffers from a number of disadvantages.

Firstly, excimer emission is a broad, structureless band so that the ability to resolve mixtures of excimers is severely limited. Furthermore the properties of excimers as specifically described cannot be "tuned" as compared to the possibility of "tuning" exciplex properties lifetime as well as emission wavelength. Consequently excimers are less versatile than exciplexes.

Secondly, the probability of exciplex or even excimer formation and detection for the proposed tandem system is expected to be very low (if it is at all possible) because of the following reasons:

a) Very high conformational flexibility of the probing groups R1 and R2 as they are proposed to be located outside the NA double-stranded helix means that the probability of the conformation required for both group to be correctly aligned to give the excimer or exciplex structure is extremely low.

b) The hydrocarbon groups (e.g. pyrene, perylene, anthracene, naphthalene etc.) which were proposed in EP-A-0 810 291 to be used as R1 or R2 labelling groups are very prone to strong hydrophobic interactions. These are likely to involve nucleotide residues and base pairs, as pointed out explicitly in EP-A-0 810 291 and which might be competitive with the exciplex/excimer forming interaction between R1 and R2 groups, thus compromising excimer/exciplex formation. This point of view is supported by the known red-field shift of $\lambda_{max}$ in the UV-visible spectra of pyrene (E. V. Bichenkova, D. S. Marks, S. G. Lokhov, M. I. Dobrikov, V. V. Vlassov and K. T. Douglas, J. Biomol. Struct. Dyn., 1997, 15, pp. 307–320) and especially of perylene groups when they are conjugated to oligonucleotides and especially after duplex formation. These results are also in good agreement with the strong 1H-NMR line broadening observed for the above probing groups in the case of pyrene and their nearest nucleotide protons for the conjugates (R1-5'p-ON1, where R1 is pyrenyl): reported by E. V. Bichenkova, D. S. Marks, S. G. Lokhov, M. I. Dobrikov, V. V. Vlassov and K. T. Douglas, J. Biomol. Struct. Dyn., 1997, 15, pp. 307–320). This is known from experimental studies to be also the case for the full system of two short oligonucleotides annealed to a longer target strand of DNA, a so-called binary system (3'-ON1-p5'-R1)+(R2-3'p-ON2)+(target DNA) (E. V. Bichenkova, D. S. Marks, S. G. Lokhov, M. I. Dobrikov, V. V. Vlassov and K. T. Douglas, J. Biomol. Struct. Dyn., 1997, 15, pp. 307–320).

c) Whilst excimer emission is solvent dependent in term of several parameters including emitted wavelength and quantum efficiency, exciplex emission is characterised by a very much more marked dependence on solvent nature. Solvent polarity is crucial to the behaviour of exciplexes and intermolecular exciplexes do not emit usually in solvents even as weakly polar as acetonitrile. Exciplex emission in intermolecular situations occurs preferentially in solvents of low polarity (J. Birks, Photophysics of Aromatic Molecules, publ. Wiley and many other sources). For strongly interacting exciplex partners, such as aromatic hydrocarbons with dialkylanilines (the most widely studied family), the exciplex arises from a partial charge-transferred state, which is sufficiently stable in nonpolar solvents to fluoresce. Increased solvent polarity preferentially solvates and stabilises charge separation and at a dielectric constant of approximately 14, the pyrene:diethylaniline pair has an exciplex absorption spectrum identical with the ion pair, pyrene$^-$:PhNEt$_2^+$. This behavioural shift has been ascribed to a change in structure for exciplexes going from compact in nonpolar solvents to loose in polar solvents (Verhoeven et al., Chem. Phys. Lett. (1987) 140, 587; Pur Appl, Chem. (1990) 62, 1585; (1993), 65, 1717).

There are some exciplex systems which are known to emit in solvents as polar as DMSO, 20% aq. acetonitrile (e.g. Lewis & Cohen, J. Phys. Chem. (1994) 98, 10591) or even water (Pal & Ghosh, J. Photochem. Photobiol. A. Chem. (1994) 78, 31), but only under special circumstances. Therefore, exciplex emission in terms analogous to those described in EP-A-0 810 291 will be prevented by the high polarity of the buffer surrounding the NA binary system because the R1 and R2 labelling groups are deliberately arranged to be located outside the NA helix structure and thus lying in bulk aqueous solvent, the usual environment of NA systems under normal experimental conditions.

d) The high polarity of the buffer system surrounding the binary DNA duplex may be expected to quench excimer emission resulting in very low detectability except in especially favourable circumstances;

Thus use of exciplexes in detection of nucleic acids would represent a considerable advance because of the advantages of being able to "tune" the emission properties of exciplexes as alluded to above. It is however clear from the aforementioned summary of the prior art that there is no disclosure as to how exciplexes may be used in the relatively high polar environment in which detection procedures for nucleic acids are usually carried out (e.g. in aqueous systems) for detection of nucleic acids.

It is therefore an object of the present invention to provide methods of nucleic acid analysis which are based on formation and detection of an exciplex.

First Aspect

According to a first aspect of the present invention there is provided a method of analysing a sample to determine the presence or otherwise therein of a target polynucleotide sequence, the method comprising (a) treating the sample under hybridizing conditions with
 i) a first polynucleotide probe having a 5'-terminal nucleotide labelled with a first chromophoric moiety able on photo-irradiation to form a complex with a second chromophoric moiety, and
 (ii) a second polynucleotide probe labelled at its 3'-terminal nucleotide with moiety, said first and second probes being adapted to bind to mutually exclusive regions of said target sequence such that said moieties are at the proximal ends of the probes and are able to form said complex which is detectably different from the first and second moieties, (b) effecting photo-irradiation to cause complex formation, and (c) detecting for formation of the complex characterised in that (d) said first and second moieties are different from each other and are capable of forming an exciplex as the detectable complex, and (e) the first and second moieties come into exciplex forming relationship in a localised region of greater hydrophobicity than the bulk phase of the sample being analysed.

For convenience in the subsequent description the polynucleotide sequences of the first and second probes are also designated as ON1 and ON2 respectively and the first and second chromophoric groups are represented respectively as R1 and R2. For convenience also the first and second probes are designated as ON-R1 and R2-ON2 respectively although it should be understood in each case that the R and ON groups may be bonded via a linker.

We have found, and this forms the basis of the first aspect of the present invention that by arranging for the R1 and R2 moieties to come into exciplex forming relationship in a localised region of greater hydrophobicity than the bulk phase then it is possible successfully to obtain exciplex emission even in the case where the bulk is a high or relatively highly polar medium, e.g. aqueous.

In accordance with a preferred embodiment of this aspect of the invention, the R1 and R2 moieties come into exciplex forming relationship within the immediate vicinity of the double stranded nucleic acid (only formed if the target sequence is present and the two probes are hybridized thereto). As such, the R1 and R2 groups are in a local hydrophobic environment favouring exciplex formation on photo-irradiation.

By "within the immediate vicinity of the nucleic acid molecule" we mean that the exciplex is formed either within the duplex structure itself or in the vicinity of the molecular surface of the nucleic acid. Generally this will imply that the exciplex is formed within 20 Å of the axis of the nucleic acid, more preferably within 15 Å of the axis, and even more preferably within 10 Å.

In general terms, positions at which exciplex formation may occur for this embodiment of the invention include (a) within the duplex structure itself for example in the manner of surrogate base pair partners with or without actual base pairing;

(b) lying at least partially within one of the grooves (e.g. the major or minor groove) of the double stranded nucleic acid structure; or (c) along or across the polyphosphate backbone.

The exciplex partners R1 and R2 are arranged to be located in the vicinity of the nucleic acid helix structure by covalent attachment to the particular sites of ON1 and ON2 and will be additionally held in this region by weak interactions e.g. electrostatic forces, hydrogen bonding. Van der Waals forces, dipole-dipole interactions, and/or hydrophobic interactions.

The R1 and R2 moieties may for example be brought into exciplex relationship within the immediate vicinity of the double stranded nucleic acid in any of the following ways (A) within or within the vicinity of the minor groove of the double stranded nucleic acid;

(B) within or within the vicinity of the major groove of the double stranded nucleic acid;

(C) into the region of the axis of the nucleic acid helix;

(D) between nucleotide base pairs;

(E) against the polyphosphate anionic and associated (deoxy)ribosyl backbone.

(F) within a cavity, bulge or distortion formed at or between the adjacent 3' and 5' ends of the oligonucleotide probes.

(The groove nomenclature referred to in (A) and (B) is that commonly used for B-DNA but analogous reasoning is understood for other forms of nucleic acid conformation including A-DNA, Z-DNA and others).

We do not however wish to imply that, on formation of the double stranded nucleic acid, the R1 and R2 moieties locate at, and only at, the required position for exciplex formation. Rather, the R1 and R2 moieties may be bonded to the probes via linkers which allow movement of the moieties outside of the double stranded nucleic acid but which are such that they are also able to move to their exciplex forming position (within the double stranded nucleic acid) and that when both moieties are located at their respective positions exciplex formation can occur. It is however also possible to use relatively "rigid" linkers which with the probes hybridised to the nucleic acid, "constrain" the moieties to be in exciplex forming relationship.

The design of the linkers referred to in the previous paragraph is well within the ability if the person skilled in the art and depends on factors such as the position at which the linkers are bonded to the probes, the position (e.g. in the minor groove) at which the R1 and R2 moieties are intended to come into exciplex forming relationship, and the structure of the double stranded nucleic acid formed an hybridisation of the probes to the target sequence, and the molecular size of the R1 and R2 moieties.

Thus for example the linkers may be designed in the basis of known 3-dimensional structure data for nucleic acids, including data for split-pair binary type complexes (see for example E. V. Bichenkova, D. S. Marks, S. G. Lokhov, M. I. Dobrikov, V. V. Vlassov and K. T. Douglas, J. Biomol. Struct. Dyn., 1997, 15, pp. 307–320) combined with the use of molecular graphics and other computational techniques known and used by those skilled in the art.

It will generally be convenient to bond at least one of the R1 and R2 moieties to groups of the probes orientated towards that region of the double stranded nucleic acid at which the first and second moieties come into exciplex forming relationship.

Thus, certain positions (such as the —$NH_2$ groups of guanosine, adenosine or cytidine, the C5 position of cytidine, uridine or 2'-deoxyuridine, the N7 position for guanosine and adenosine, and the N3 position of cytidine and adenosine etc) may be used as potential sites for the attachment of the R1 and R2 probing groups to position them in the required orientation (in the minor or major groove, or between nucleotide base pairs, or in the position of the omitted nucleotide base(s) for the case(s) in which a gap is introduced (infra) or against the polyphosphate anionic and associated (deoxy)ribosyl backbone.

There are however many other possibilities for attachment of the exciplex partners to the ON probes, e.g. to O3', 5' or 2' —OH groups (sugar ring) or to a phosphate group.

Purely by example, the first moiety may be covalently attached to the terminal 5'-phosphate group of the first probe a —CH$_2$—NH— linker group and the second moiety may be bonded to an appropriately directed group (e.g. amino group) of the second probe via a —C$_2$—CO—NH—(CH$_2$—NH—)$_2$ linker group. There are however, very many alternatives possible to both linker positions on the probe oligonucleotides and in the chemical composition of the linker group itself.

In accordance with this first embodiment, it is preferred that with the first and second probes hybridized to the target sequence, there is at least one base but preferably no more than 3 bases of that sequence between the proximal ends of the probes, i.e. a base or bases to which the probes are not hybridized. This "gap" between the probes provides a number of advantages.

Firstly, the "gap" provides a hydrophobic pocket to enable the R1 and R2 moieties to be located within the double stranded structure.

Secondly, the "gap" avoids a disadvantage we have recognised with regard to the procedure of EP-A-0 810 291 in which the two probes are in continuous alignment (i.e. there is no "gap"). The continuous alignment of ON1-R1 and R2-ON2 on the target nucleic acid (without any gap between ON1-R1 and R-2-ON2 probes) results in a cooperative increase in the hybridization stabilisation of ON1-R1 with target NA caused by the presence of the other short oligonucleotide, R2-ON2 (Pyshnyi D. V., Pyshnaya I. A., Lokhov S. G., Podyiminogin M. A., Ivanova E. M., Zaryitova V. F./Pure and Applied Chemistry, 1996, Vol.68, No 6, pp. 1321–1328; Pyshnyi D. V., Pyshnaya I. A., Lokhov S. G., Podyiminogin M. A., Ivanova E. M., Zaryitova V. F./Bioorganicheskaya Khimiya, 1995, Vol.21, No.9, pp. 709–716). This means that the weakening effect on duplex stability caused by mismatches in the base-pairing for one oligonucleotide (say, ON1) with target NA sequence will be significantly diminished by the presence of an adjacent second oligonucleotide (say, ON2). (This is also true for the reverse situation in which a mismatch or even two mismatches between ON-R2 and its target sequence are less destabilising in the presence of annealed ON-R1 than in its absence). The result of this is that mutation or error sites may not be detected by the method of EP-A-0 810 291.

The provision of the gap prevents cooperative stabilization of hybridization of ON1 and ON2 with target sequence of NA. Therefore even a single mismatch in the base-paring of ON1 or/and ON2 with the target sequence of NA will be crucial for complex formation and even a single mutation will be detectable by this method.

Thirdly, provided that there is a "gap" of two or more nucleotides in the target sequence, the R1 and R2 moieties may be designed to substitute for nucleotide residues (with or without hydrogen bonding to the unpaired base sites in the gap region of the duplex structure (or helix structure) in such a way as to form a stacking arrangement on top of each other and the bases at the innermost ends of their respective oligonucleotide probes ON1 and ON2 or on top of one another whilst lying in the major or minor groove or along the surface of the duplex.

In accordance with a second embodiment of the first aspect of the invention, an additive may be incorporated in the sample for providing the localised region of increased hydrophobicity.

In accordance with this embodiment of the invention, the R1 and R2 moieties may (but not necessarily) come into exciplex forming relationship external to the double stranded nucleic acid (as opposed to "within" for the method of the previous embodiment). The use of the additive allows an exciplex signal to be developed even for the case where the bulk phase of the sample is aqueous.

Examples of additives which may be included in accordance with this embodiment of the invention include compounds capable of acting as a host in a host-guest complex for which the guest is formed of the R1 and R2 moieties in exciplex forming relationship. The host compound may be one having a cavity in which the guest is received. The type of cavity that can be added as external agent to develop the exciplex fluorescent signal include cyclodextrins, cyclophanes, calixarenes, crown ethers, cryptands and other well known host-guest systems or analogues or mixed structures capable of providing a hydrophobic cavity able to sequester wholly or partially the exciplex partners in an exciplex forming relationship.

Cyclodextrins are known from studies on intramolecular exciplex assemblies to enhance exciplex emission in aqueous solution (G. S. Cox et al. JACS (1984) v106, p422 et seq.) depending on whether the cyclodextrin is $\alpha$, $\beta$ or $\gamma$ and on the pH of the solution. To use the cyclodextrin method the binary split-probe system consisting of the target strand and the 2 shorter complementary oligos chemically modified with the exciplex partners has added to it $\alpha$, $\beta$, $\gamma$, or other cyclodextrin, as is appropriate for the particular pair of exciplex partners (the particular cyclodextrin cavity size depends on the particular pair of partners being used).

Cyclophanes, calixarenes, crown ethers and many other examples from the families of host-guest chemistry can also serve as additives that provide a cavity in the manner of cyclodextrin. An example of such a cyclophane exciplex system is described in D. R. Benson & J. Fu, Tetrahed. Lett. (1996) v37 pp4833–4836. To use the cyclophane method, the binary split-probe system consisting of the target strand and the 2 shorter complementary oligos chemically modified with the exciplex partners has added to it a cyclophane appropriate for the particular pair of exciplex partners (the particular cyclophane cavity size being constructed for the particular pair of partners being used).

Alternatively, the additive may for example be a surface active agent which in the bulk phase forms aggregates (e.g. micelles) within which the R1 and R2 groups may come into exciplex forming relationships. The surface active agent is preferably a cationic surface active agent, most preferably a quaternary ammonium salt having at least one chain of 4 or more carbon atoms bonded to the quaternary nitrogen atom. Preferably this carbon chain has at least 8 and even more preferably at least 10 carbon atoms. Preferably also the quaternary ammonium salt has at least two, and preferably three, $C_{1-3}$ alkyl groups, particularly methyl groups. The preferred quaternary ammonium cations include the hexadecyltrimethyl ammonium, cetyldimethylethyl ammonium, tetradecyltrimethyl ammonium, decyltrimethyl ammonium and dodecyltrimethyl ammonium ions. The anion is preferably bromide. The concentration of the surface active agent is preferably $1 \times 10^{-5}$ to $1 \times 10^{-6}$ M although we do not preclude amounts outside this range provided that the amount used is not so high as to precipitate the nucleic acid.

Second Aspect

The feature of providing for exciplex formation within the immediate vicinity of the double stranded nucleic acid forms an important aspect of the invention in its own right and therefore according to a second aspect of the present invention there is provided a method of analysing a sample to determine the presence or otherwise therein of a target polynucleotide sequence, the method comprising (a) treating the sample under hybridizing conditions with
   (i) a first polynucleotide probe having a 5'-terminal nucleotide labelled with a first chromophoric moiety able on photo-irradiation to form a complex with a second chromophoric moiety, and
   (ii) a second polynucleotide probe labelled at its 3'-terminal nucleotide with moiety, said first and second probes being adapted to bind to mutually exclusive regions of said target sequence such that said moieties are at the proximal ends of the probes and are able to from said complex which is detectably different from the first and second moieties, (b) effecting photo-irradiation to cause complex formation, and (c) detecting for formation of the complex characterised in that (d) said first and second moieties are different from each other and are capable of forming an exciplex as the detectable complex, and (e) the first and second moieties come into exciplex forming relationship within the immediate vicinity of the double stranded nucleic acid.

The location at which the exciplex is formed in accordance with this second aspect of the invention (e.g. within the duplex structure itself lying at least partially within one or more of the grooves, or along or across the polyphosphate backbone) may be as described more fully under the first aspect of the invention.

Third Aspect

According to a third of the present invention there is provided a method of analysing a sample to determine the presence or otherwise therein of a target polynucleotide sequence, the method comprising (a) treating the sample under hybridizing conditions with
   i) a first polynucleotide probe having a 5'-terminal nucleotide labelled with a first chromophoric moiety able on photo-irradiation to form a complex with a second chromophoric moiety, and
   (ii) a second polynucleotide probe labelled at its 3'-terminal nucleotide with moiety, said first and second probes being adapted to bind to mutually exclusive regions of said target sequence such that said moieties are at the proximal ends of the probes and are able to form said complex which is detectably different from the first and second moieties, (b) effecting photo-irradiation to cause complex formation, and (c) detecting for formation of the complex characterised in that (d) said first and second moieties are different from each other and are capable of forming an exciplex as the detectable complex, and (e) there is included in the sample being analysed at least one compound capable of developing an exciplex fluorescent signal when the first and second moieties are in exciplex forming relationship.

In accordance with this (third) aspect of the invention, the first and second moieties may come into exciplex forming relationship external to the double stranded nucleic acid. In such a case, the use of the additive allows an exciplex signal to be developed even for the case where the bulk phase of the sample in water. It is however also possible in accordance with this aspect of the invention for the exciplex to be formed within the immediate vicinity of the nucleic acid as described for the first aspect of the invention.

Examples of additives which may be included in accordance with this aspect of the invention include compounds capable of acting as a host in a host-guest complex for which the guest is formed of the first and second moieties in exciplex relationship. The host compound may be one having a cavity in which the guest is received. The type of cavity that can added as external agent to develop the exciplex fluorescent signal include cyclodextrins, cyclophanes, calixarenes, crown ethers, cryptands and other well known host-guest systems. Examples of host as described more fully for the first aspect of the present invention are applicable also to the second aspect of the invention. However in accordance with this aspect it is not essential that the host provides a localised hydrophobic environment for the exciplex partners.

It is known that exciplexes in water can stabilized by polyanions. Consequently in a further embodiment of this aspect, the additive may be a polyanion.

The polymer may, for example, be a polysulfate such as poly(vinyl sulfate), chondroitin sulfate A, B or C, heparin, a polyphosphate, a nucleic acid or semi-synthetic nucleic acid (including PNA's and peptide nucleic acids), a polycarboxylate, or a polyanionic polymer containing at least two of carboxylate, phosphate and sulfate groups.

The amount of polymeric species added is such as to develop the exciplex fluorescence emission and typically is an excess of approximately 4 to 16-fold over the concentration of the shorter split-probe oligos bearing the exciplex partners.

In accordance with this embodiment, the moieties R1 and R2 may be of the formula

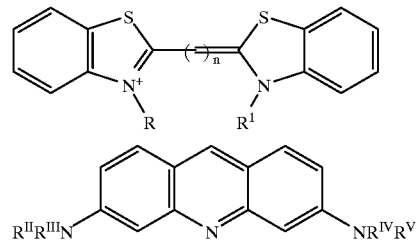

where R, $R^1$, $R^{11}$, $R^{111}$, $R^{IV}$ and $R^V$ are alkyl groups, preferably methyl or ethyl, and n is an odd integer.

An exciplex can be formed from excited 3,3'-diethylthiacyanine iodide (TH1A) ($R=R^1=Et$; n=1) and cool acridine orange $R^{11}=R^{11}=R^{IV}=R^V=Me$ can only be detected in the presence of polyanions.

Pal & Ghosh J. Photochem. Photobiol. A. Chem. (1994) 78, 31 showed that the exciplex formed by 3,3"-diethylthiacyanine iodide (TH1A) and acridine orange (AO) in the presence of chondroitin sulphates A, B or C emits at approximately 560 nm. On excitation at 490 nm ($\lambda_{max}$ for AO) the intensity of emission is greatly reduced compared to excitation at 420 nm ($\lambda_{max}$ TH1A absorption) and $\lambda_{max}$ for emission shifts from 560 to 522 nm: the latter is the $\lambda_{max}$ for fluorescence emission of AO. The exciplex is formed by excitation of THIA with cool AO (not with excited AO, cool THIA). They also showed that the enhancement of THIA fluorescence by the matrix depends also on structure of the polyanionic matrix (chondroitin sulphate C is about 4 times as effective chondroitin sulphate A). DNA enhances THIA fluorescence twice as strongly as chondroitin sulfate C. They also showed that heparin facilitates exciplex formation in the aqueous environment of THIA bound to a polymer. The synthetic polymer poly(vinylsulphate) (PVS) quenches the monomer fluorescence of AO completely but facilitates the exciplex emission between THIA and AO ($\lambda_{emission}$=560 nm).

We have measured the emission of the acridine orange: thiacyanine system and found that addition of PVS does indeed enhance fluorescent emission so that detection is convenient in water.

In addition we were able to show that the fluorescence does not arise from fluorescence of a charge transfer complex between the acridine and the thiacyanine whose ground state becomes photo-excited and fluoresces, thus establishing the exciplex nature of the emission.

1. Further improvements can be achieved by the use of thiacyanines with longer C bridges (see below) or other compounds which can be used to shift exciplex emission to even greater wavelengths with the appropriate partner.

The following table illustrates the relationship between n and $\lambda_{max}$ in the above compound.

| n= | $\lambda_{max}$ (absorption of dye) |
|---|---|
| 1 | 424 nm |
| 3 | 560 |
| 5 | 655 |
| 6 | 765 |

Fourth Aspect

According to a fourth aspect of the present invention there is provided a method of analysing a sample to determine the presence or otherwise therein of a target polynucleotide sequence, the method comprising (a) treating the sample under hybridizing conditions with
   i) a first polynucleotide probe having a 5'-terminal nucleotide labelled with a first chromophoric moiety able on photo-irradiation to form a complex with a second chromophoric moiety, and
   (ii) a second polynucleotide probe labelled at its 3'-terminal nucleotide with moiety, said first and second probes being adapted to bind to mutually exclusive regions of said target sequence such that said moieties are at the proximal ends of the probes and are able to form said complex which is detectably different from the first and second moieties, (b) effecting photo-irradiation to cause complex formation and (c) detecting for formation of the complex characterised in that (d) said first and second moieties are different from each other and are capable of forming an exciplex as the detectable complex, and (e) a magnetic field is applied to enhance exciplex emission.

The fourth aspect of the invention this involves the application of a magnetic field to enhance exciplex emission. This allows exciplex emission to be produced even in polar solvents. The magnetic field may for example be up to 5 T, more preferably up to 2 T, e.g. up to 1 T.

In accordance with this (fourth) aspect of the invention, the first and second moieties may come into exciplex forming relationship external to the double stranded nucleic acid. In such a case, the use of the additive allows an exciplex signal to be developed even for the case where the bulk phase of the sample in water. It is however also possible in accordance with this aspect of the invention for the exciplex to be formed within the immediate vicinity of the nucleic acid as described for the first aspect of the invention.

The increase in exciplex luminescence with the magnetic field will depend on factors such as (a) the particular exciplex partners, (b) the particular solvent (or solvent mixture), (c) the magnetic field strength, and the ionic strength of the bath media.

Examples of exciplex partners which may be said to be used in accordance with this aspect of the invention includes (i) Phenanthrene and Dimethyl Aniline, and (ii) Pyrene and Dimethyl Aniline.

Thus it is proposed that the split-probe exciplex pair is set up as described above and an external magnetic field applied: the magnitude of the field must be optimised, along with the solvent mixture used in the case of mixed solvents and also the ionic strength.

Fifth Aspect

According to the fifth aspect of the present invention there is provided a method of analysing a sample comprised of a relatively polar medium to determine the presence or otherwise therein of a target polynucleotide sequence, the method comprising (a) treating the sample under hybridizing conditions with
   i) a first polynucleotide probe having a 5'-terminal nucleotide labelled with a first chromophoric moiety able on photo-irradiation to form a complex with a second chromophoric moiety, and
   (ii) a second polynucleotide probe labelled at its 3'-terminal nucleotide with moiety, said first and second probes being adapted to bind to mutually exclusive regions of said target sequence such that said moieties are at the proximal ends of the probes and are able to form said complex which is detectably different from the first and second moieties, (b) effecting photo-irradiation to cause complex formation, and (c) detecting for formation of the complex characterised in that (d) said first and second moieties are different from each other and are capable of forming an exciplex as the detectable complex, and in that (e) the method involves at least on of the steps, in either order, of (i) at least partial removal of the relatively polar medium, and (ii) addition of a less polar medium thereby to enhance exciplex emission.

This aspect of the invention is applicable particularly (but not exclusively) in the case where the relatively polar medium is water.

In accordance with this (fifth) aspect of the invention, the first and second moieties may come into exciplex forming relationship external to the double stranded nucleic acid. In such a case, the use of the additive allows an exciplex signal to be developed even for the case where the bulk phase of the sample in water. It is however also possible in accordance with this aspect of the invention for the exciplex to be formed within the immediate vicinity of the nucleic acid as described for the first aspect of the invention.

In accordance with the a first embodiment of this aspect of the invention, the relatively polar medium is at least partial removed from the sample, e.g. by vacuum or other dehydration technique (e.g. freeze drying). Depending on factors such as the particular exciplex partners, this (at least) partial removal of the relatively polar medium may be sufficient to give the required exciplex emission (given that the oligonucleotides have hybridized to the target nucleic acid). It is however possible, in accordance with this embodiment, to add to the (at least partially) dehydrated sample a solvent or solvent mixture which is less polar than the original medium. Thus of example, is the case where the original medium was water, the relatively less polar solvent may comprise acetonotrite or even lower polarity solvent such as methylcyclohexane. Mixtures of each solvents may also be used.

In accordance with a second embodiment of this aspect it is possible to add to the sample (without prior removal of the original bulk medium) a solvent or solvent mixture of lower polarity than the original bulk medium. Examples of such solvents and solvent mixtures are as described for the first embodiment.

Depending on factors such as the exciplex partners, the addition of the solvent or solvent mixture may be sufficient to provide the required exciplex emission (given that the oligonucleotides have hybridized to the target nucleic acid).

General Considerations

Exciplexes for use in any one of the above aspects of the invention may be as disclosed, for example, by "The Exciplex" (A. Weller; ed M. Gordon and W. R. Ware, Academic Press N.Y. 1975) and Z. Phys. Chem (1970) 69 1983. There are very many more specific examples in the literature and these include pyrene and an N,N-dialkyl amine, perylene and an N,N-dialkyl amine, a metalloporphyrin and a nitroaromatic compound (see J. Amer. Chem. Soc. (1971), 93, 7093; (1974), 96 (6349), and between a phthalocyanine and a nitroaromatic (see Inorg. Chem., (1983) 22, 1672).

The methods of the various aspects of the invention should not be considered as mutually exclusive and the aspects may be employed in any combination. Thus, purely by way of example, a method as carried out in accordance with the first embodiment of the first aspect (i.e. the formation of the exciplex within the immediate vacinity of the nucleic acid molecule) may be used in conjunction with the method of the fourth aspect i.e. application of a magnetic field to enhance exciplex emission. Other combinations of aspect are, of course, also possible.

The methods of the invention are conducted under hybridizing conditions to ensure that the oligonucleotide probe would hybridize to the target nucleic acid (if present) to allow exciplex formation. Such hybridization conditions are well known to those skilled in the art and generally require buffers, concentrations and/or temperature conditions appropriate to the length of the oligonucleotide probes and/or the particular basis present therein.

The methods of all aspects of the invention are particularly applicable to the formation, and detection or exciplexes in aqueous systems.

It is particularly preferred for all aspects of the invention that the adjacent 3' and 5' ends of the oligonucleotide probes bond to the target nucleic acid with at least one (and preferably no more than three) basis of that target therebetween. For all aspects of the invention the provision of this gap provides the advantages detailed under the first aspect of the invention, particularly with regard to preventing co-operative stabilisation of hybridization of the two oligonucleotide probes with the target sequence.

It is a feature of the invention that the structure of the binding site govern the interaction of the two precursor components of the complex which are to be constrained in a position at, or from, which complex formation can inevitably occur. This will typically imply that (after the binding event has occurred) the precursor components of the complex may be constrained to be within 1 nm e.g. within 0.6 nm or even 0.5 nm, or such distance as represents the thermodynamically favoured equilibrium structure of the exciplex.

This provides for high specificity, overcomes problems with "background" and is in contrast to the preferred embodiment of U.S. Pat. No. 5,332,659 in which there is a (difficult to measure) small decrease in signal when binding has occurred.

The requirements for the juxtaposition of the R1 and R2 moieties for formulation of a exciplex may be achieved from a knowledge of the 3-dimensional molecular structure of the predetermined region of the nucleic acid to be investigated and by designing (if necessarily empirically) the investigation technique such that the precursor components of the R1 and R2 moieties are constrained to be within the required distance. Knowledge of the 3-dimensional molecular structure of the nucleic acid may be obtained from techniques such as nuclear magnetic resonance in combination with the molecule modelling and X-ray diffraction studies) and other structural methods.

The method of the invention may be used qualitatively for detecting the presence of a particular nucleic acid in a sample and/or quantitatively for detecting the amount thereof. In the former case, the presence of a detectable signal demonstrates the macromolecule is present in the sample and in the latter case the level of the signal is representative of the amount of the nucleic acid present.

The invention is applicable particularly to the detection of nucleic acid in single standard form but is also applicable to the detection of nucleic acids in double stranded form of even higher order structure, e.g. triplexes.

The invention may be applied particularly to the analysis of DNA, RNA, a mixed RNA:DNA hybrid or a PNA (protein or peptide nucleic acid) as the nucleic acid to be investigated. The method may be applied to the analysis of nucleic acids (e.g. DNA/RNA) in combination with other molecules such as proteins, and may also be applied to the detection of nucleic acids (e.g. DNA) in chromosones, chromotin and higher cellular structures.

The method may be effected using a pair of oligonucleotide probes which (a) are each labelled with a precursor component of the exciplex.

(b) are capable of binding close by adjacent to each other along a predetermined sequence of the nucleic acid strand, preferably such that their adjacent 5' and 3' ends are within 3 bases (of the nucleic acid strand) from each other and are ideally separated by at most three (e.g. 1, 2 or 3) bases; and (c) when bound to the nucleic acid strand as under (b) their respective complex precursor components are positionally constrained so as to be able to form the detectable complex.

For such an assay, the length of the oligonucleotide probes should be such that there is sufficient "binding affinity" to the nucleic acid that the probes do not become denatured from the target strand as a result of interactions occurring during complex formation and that when both probes are annealed to the target in a contiguous manner a unique stretch of DNA can be reasonably predicted to be sequestered e.g. in a preparation of the genome of a human cell or cells. Generally each oligonucleotide probe (typically a combination of two or more) will comprise at least 6 and preferably up to 9 or even more bases.

As applied to the analysis of nucleic acids, the method of invention may be used to detect the presence and/or amount of particular nucleic acid in a sample or may be used to test for the presence of a mutation in nucleic acid (e.g. the probes may be of a sequence such that at least one probe will only bind to the stand if the mutation is present so that no exciplex emission would be observed). The invention may, for example, be aimed at biological exploitation such as detecting specific diagnostic sequences, and with sufficiently sensitive detection, at single cell events such as the real-time formation of recombination sites in DNA, RNA or chromosomes.

Detection of the exciplex may be by means of wavelength detection but is more preferably by the use of time resolved fluorescence or by a combination of these approaches. Exciplexes may also be detectable by other spectroscopic methods including circular dichroic spectral effects as has been described for excimer systems (see for example H. Mihara, Y. Tanaka, T Fujimoto, and N. Nishino J. Chem. Soc. Perkin Trans 2 (1995) p1133–1140.

It is possible for the analysis to be such that more than one type of exciplex may be formed whereby the various types of exciplex are separately detectable to identify particular aspects of the nucleic acid under investigation. Thus for example the method may involve formation of two or more exciplexes which are detectable at different wavelengths. More preferably however detection of the different exciplexes will be by means of time resolved fluorescence or by a combination of wavelength dependent and time resolved methods.

The method of the present invention may involve an analysis for determining a characteristic lifetime of an exciplex using the technique described more fully in our co-pending application PCT/GB99/02047 entitled "Sample Analysis", the disclosure of which is incorporated herein by reference. More particularly, the technique of the co-pending application is a method of analysis for determining a characteristic lifetime of a sample, the method comprising exciting active elements in the sample either continuously or using pulses having an inter-pulse separation which is of the order of or less than the characteristic lifetime of the active elements, detecting quanta emitted by the active elements in the sample to obtain a detected signal, correlating the detected signal with itself and analysing the correlated signal to derive the characteristic lifetime, wherein the number of active elements in the sample and the intensity of the excitation are such that quanta are detected in a stream in which individual quanta are distinguishable from each other. As applied to the present invention, the sample is an exciplex.

The technique of the present invention may be effected using exciplexes whereof the periodicity has been altered using the techniques disclosed in our co-pending application PCT/GB99/02047 entitled "Modification of Dyes and Lifetimes of Markers", the disclosure of which is incorporated herein by reference. The co-pending application covers a method of altering the periodicity of a dyestuff by altering the lifetime of at least one lower energy state of the dyestuff by the alteration of the dyestuff's environment by means which include chemical and/or physical means. As applied to the present invention, the dyestuff is an exciplex.

In the case where two or more exciplexes are formed, electromagnetic energy emitted from one exciplex may be transmitted by resonance energy transfer to effect formation and/or detection of another type of exciplex.

Figure 2:
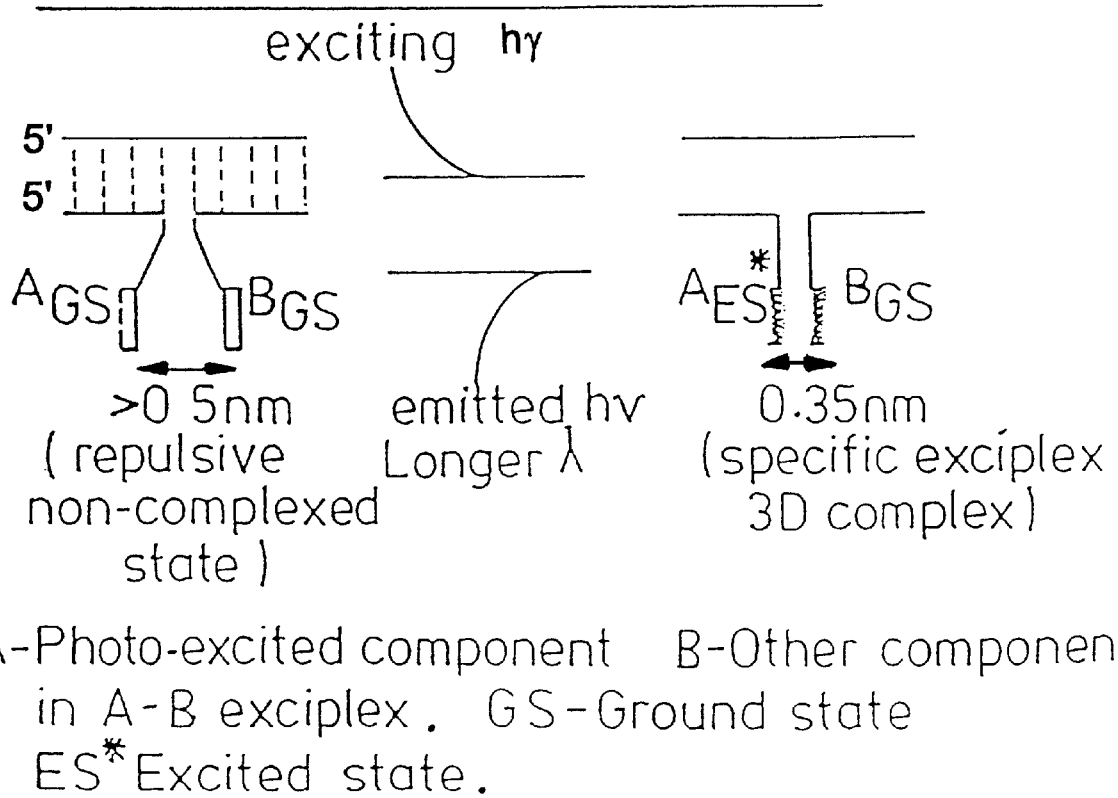
Figure 4:
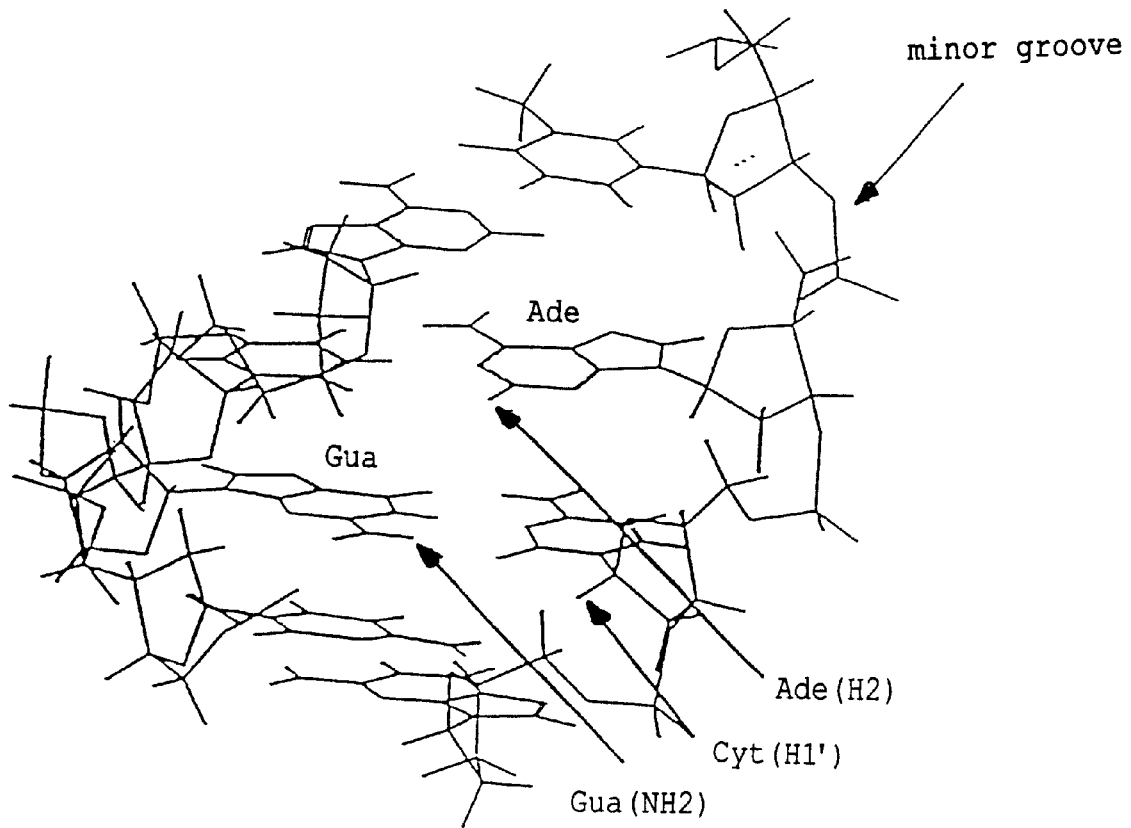
Figure 5:
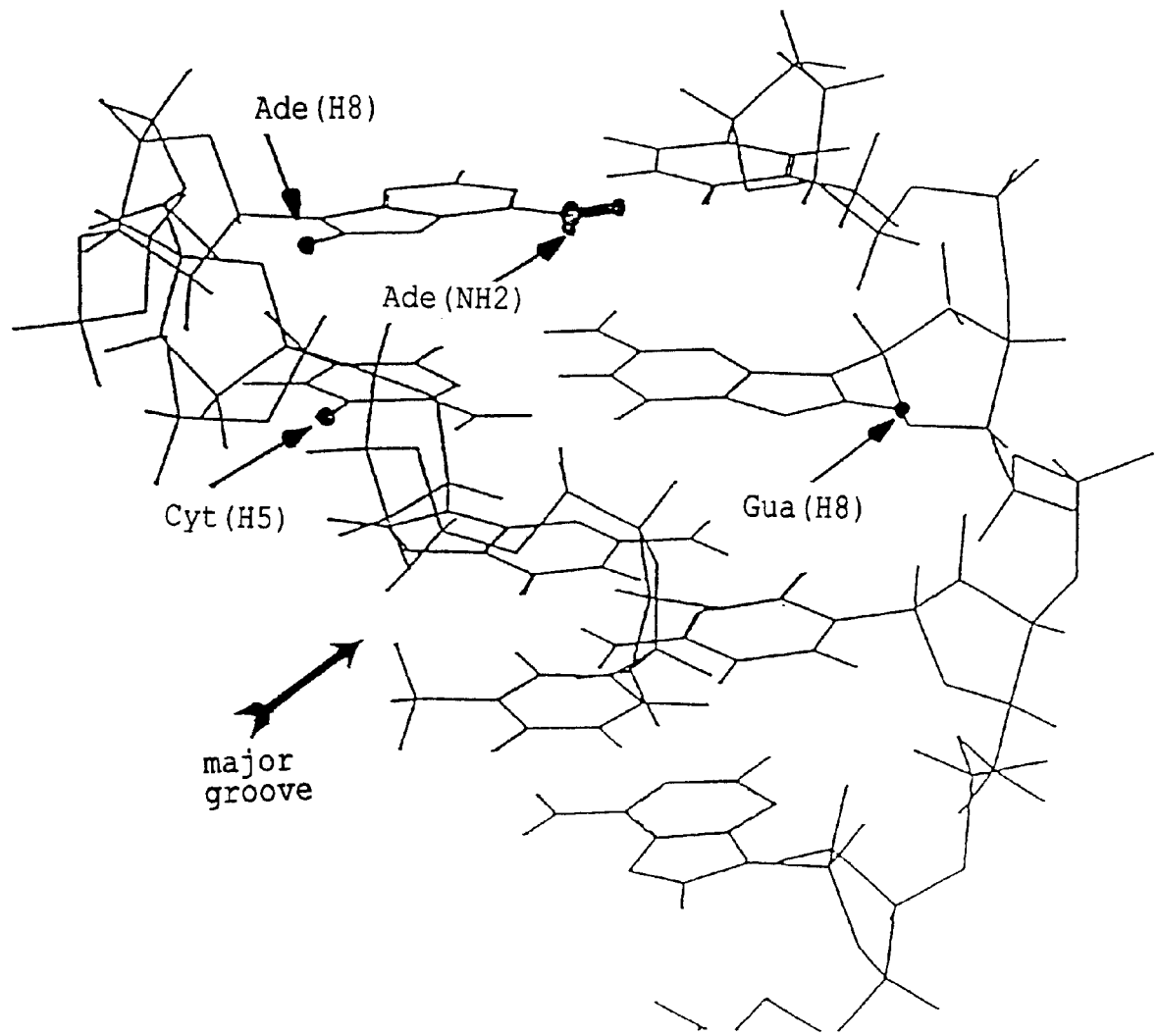
Figure 7:
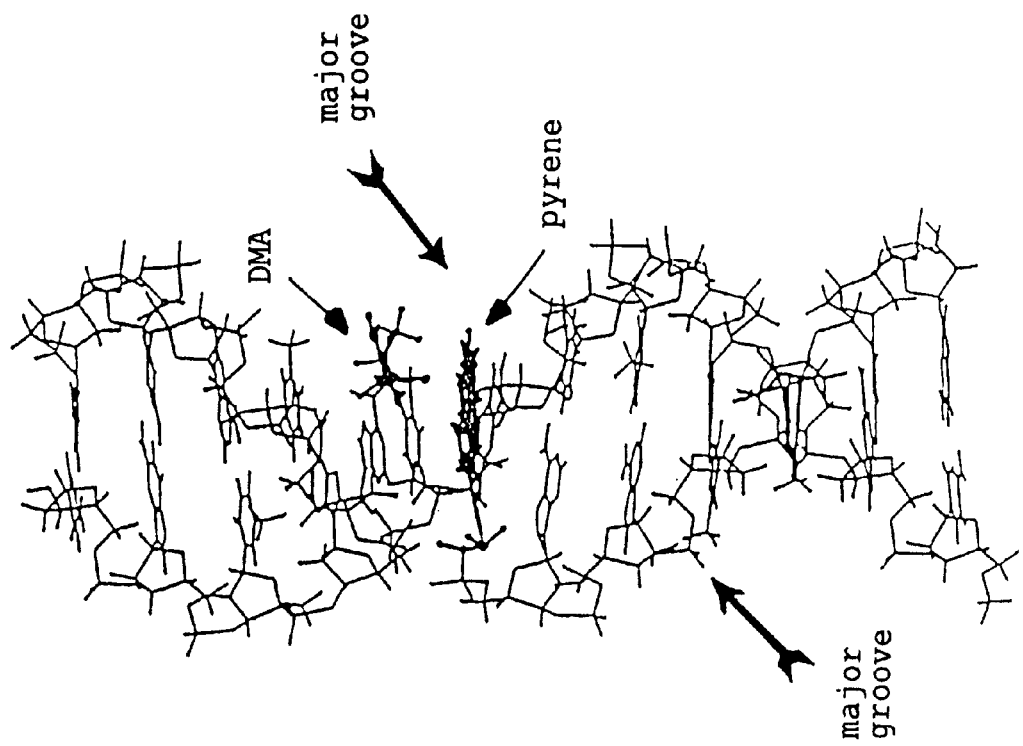
Figure 6:
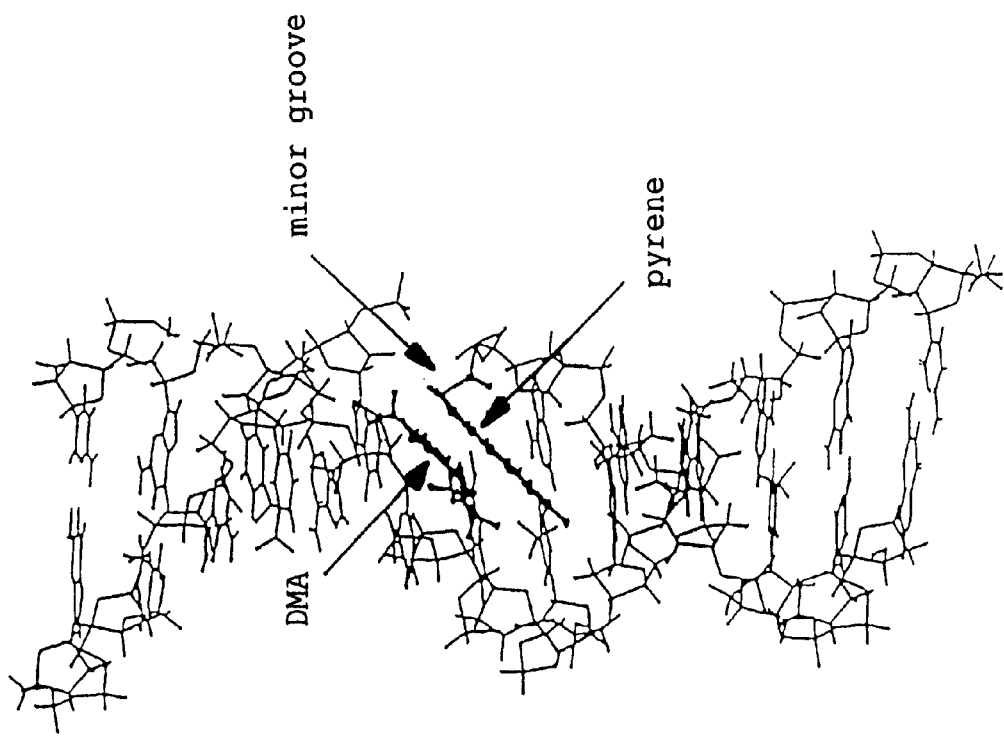
Figure 8:
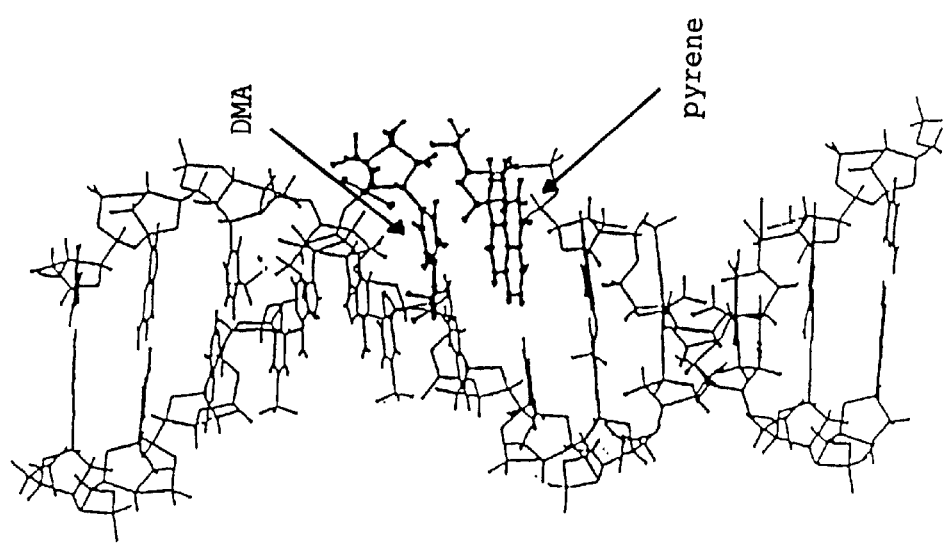

The invention will be further described by way of example only with reference to the accompanying drawings, in which FIGS. 1 and 2 schematically illustrate methods in accordance with the various aspects of the invention;

FIGS. 3A and 3B are a comparison of methods involving continuous and non-continuous alignment of oligonucleotides;

FIGS. 4 and 5 indicate examples of chemically significant nucleotide sites for attachment of exciplex forming partners in accordance with the first aspect of the invention;

FIGS. 6–8 illustrate energy minimized structures for various double stranded constructs with the exciplex forming partners being in exciplex forming relationship.

Figure 12:
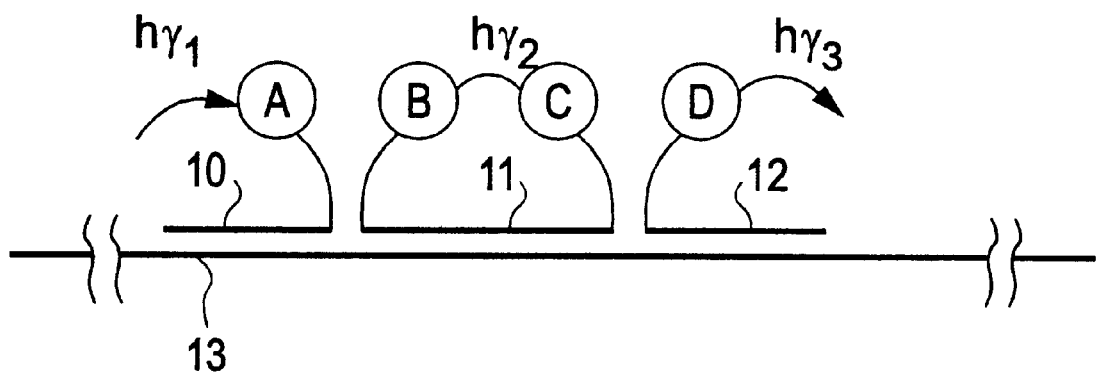

FIGS. 9, 10(a)–10(c) and 11(a) and 11(b) schematically illustrate incorporation of exciplex partners within a nucleic acid molecule; and FIG. 12 illustrates a development of the technique illustrated in FIG. 1.

FIG. 1 illustrates one embodiment of the invention in which a macromolecule in the form of a strand 1 of DNA with a binding site referenced as 2 to which two oligonucleotide probes 4 and 6 are capable of hybridizing with their adjacent 3' and 5' ends separated by a single base (represented by short vertical lines) of the strand 1. By suitable structural alteration this extra single base can be omitted so that complete complementary is achieved.

Precursor components A and B of an exciplex are bonded via respective linker groups 7 and 8 to the nucleotide at the 5' end of probe 4 and the nucleotide at the 3' end of probe 6 respectively. The nucleotide composition and the 3-dimensional configuration of the binding site 2 and the nature of the linker groups 7 and 8 are such that with probes 4 and 6 hybridized to binding site 2, the precursor components A and B which repel each other in their non-complexed state are positionally located so as inevitably to form an exciplex upon photo-excitation of component A, the exciplex then dissociating with emission of electromagnetic radiation of longer wavelength than the exciting radiation (see FIG. 2).

Signal development can only occur or can be discriminated by the time resolved detectors when A and B are very close (e.g. less than 0.4 nm) which ensures the final correct assembly of the active detector. Thus non-target sequences annealing only to probe 4 or probe 6 would be silent.

Figure 3:
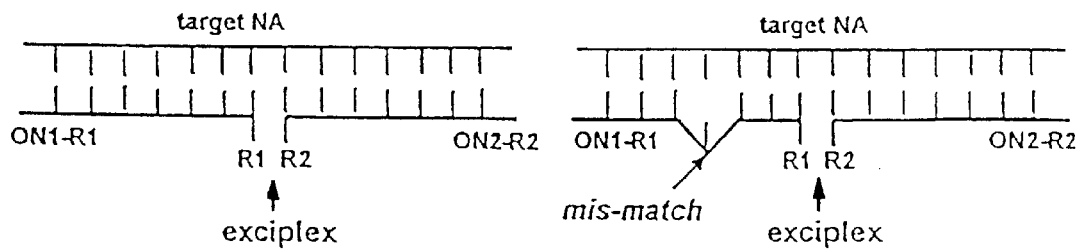
Figure 3:
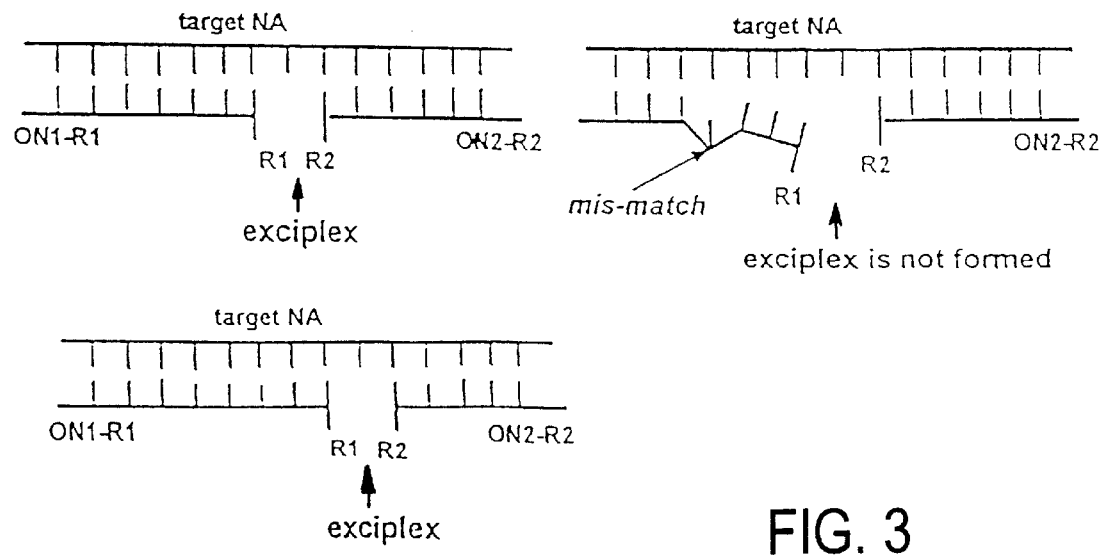

Reference is now made to FIG. 3 which, in part A thereof, illustrates a nucleic acid detection technique utilised oligonucleotide primers (ON1 and ON2) hybridizing in continuous alignment to a target strand (NA). As shown in FIG. 3A(a), there is perfect binding without mismatches. However as shown in FIG. 3A there is a one-base mismatch between oligonucleotide probe ON1 and the target. Ideally therefore ON1 will not hybridise to the target so that no exciplex will be generated. However, the continuous alignment of ON1 and ON2 results in a co-operative increase in this hybridisation stabilisation of ON1 with target NA caused by the presence of the other short oligonucleotide ON2. As a result, primer ON1 is able to bind to the target resulting in generated of an exciplex, i.e. a "false positive".

In contrast, as shown in FIG. 3B, there is non-continuous alignment of ON1 and ON2 (such that there is a "gap" of one or more nucleotides in the target NA between the proximal ends of primers ON1 and ON2). FIG. 3B(a) shows perfect binding without mis-matches. FIG. 3B(b) shows non-perfect binding with a single mis-match for ON1. The presence of the gap means that the binding of ON1 is not stabilised by ON2 especially if working at a temperature $>>T_m$ for ON1.

Consequently in the case of a one-base mismatch hybridisation between NA and ON1 the latter does not bind (or only binds partially or incorrectly) to the former so that an exciplex is not formed. The provision of the "gap" may however require the use of a second set overlapping oligonucleotide primers ON1' and ON2' (as depicted at the foot of FIG. 3) to identify the base in the original "gap".

FIG. 4 illustrates a portion of a double stranded nucleic acid structure illustrating examples off chemically active nucleotide residue groups with potential as sites for attachment of R1 and/or R2 probing agents. More particularly, the groups identified in FIG. 4 are Gua($NH_2$), Cyt(H1') and Ade(H2) which are exposed to the double stranded DNA/RNA minor groove. The R1 and/or R2 groups may be bonded via linkers) to these sites as to be in exciplex forming position in the minor groove.

FIG. 5 is similar to FIG. 4 but illustrates examples of chemically active nucleotide groups exposed to the DNA/RNA major groove. More particularly, the groups illustrated in FIG. 5 are the Ade($NH_2$) Cyt(H5), Gua(H8) and Ade(H8) groups which may be used for bonding R1 and/or R2 groups so that the latter are in exciplex forming position in the major groove.

A specific example of a binary tandem system with the R1 and R2 groups orientated to lie within the minor groove may be represented by the following system:

(target DNA)+(ON1-R1)+(R2-ON2)

where target DNA=5'-CGAATTGCATGC, ON1=5'-AATTCG and ON2=5'-GCATG. Oligonucleotides ON1 and ON2 are designed to be complementary to the neighbouring sites of target DNA and when hybridized to the target DNA stretch provide a duplex with a gap of one nucleotide residue:

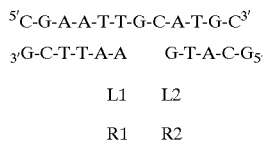

R1 is here (by way of example only) a pyrene group covalently attached to the terminal 5'-phosphate group of the ON1 via a —CH—$_2$NH— linker group (L1). R2 is (by way of example only) a dimethylaminoaniline group covalently attached to the C2-amino group of 3'-terminal guanosine nucleotide residue via —$CH_2$—CO—NH—$(CH_2)_2$—NH— linker group (L2). Molecular mechanics and dynamics calculations of this system show the pyrene group, covalently attached to the terminal 5'-phosphate group, to be located within the DNA minor groove. The guanine C2-amino group points into the minor groove, ensuring the location of R2 in the close vicinity to the R1. The result of calculation of the energy minimized structure (SYBYL 6.2, Kollman-All force field) of the complete system above is presented in FIG. 6 and shows the close juxtaposition of R1 and R2 favouring exciplex formation.

A specific example of a binary system with R1 and R2 oriented into the major groove may be represented by the following system:

(target DNA)+(ON1-R1)+(R2-ON2)

where target DNA is here=5'-CGAATTGTATGC, ON1=5'-AATTCG and ON2=5'-GCATA. Oligonucleotides ON1 and ON2 are designed to be complementary to the neighbouring sites of target DNA with a gap of one nucleotide residue.

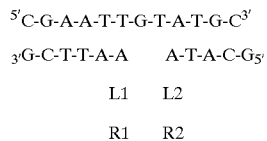

R1 is here a pyrene group covalently attached to the terminal 5'-phosphate group of the ON1 via a —$CH_2$—NH— linker group (L1). R2 is a dimethylaminoaniline group covalently attached to the C6-amino group of 3'-terminal adenosine nucleotide residue via a —$CH_2$—CO—NH—$(CH_2)_2$—NH— linker group (L2).

Molecular mechanics and dynamics calculations of this system show the pyrene group, covalently attached to the terminal 5'-phosphate group, to be located in the DNA major groove. The adenosine C6-amino group points into the helix major groove ensuring the location of R2 in the close vicinity of R1. The result of calculation of the energy-minimized structure (SYBYL 6.2, Kollman-All force field) of the complete system above is presented in FIG. 7 and shows the close juxtaposition of R1 and R2 favouring exciplex formation.

A specific example of a binary system where the probing groups R1 and R2 are designed to substitute for nucleotide residues (with or without hydrogen bonding to the unpaired base sites in region corresponding to the gap region of the target strand) and are located in stacking positions may be represented by the following system.

(target DNA)+(ON1-R1)+(R2-ON2)

where target DNA=5'-CGAATTGCATGC, ON1=5'-R1-ATTCG and ON2=5'-GCATG-R2. Oligonucleotides ON1 and ON2 are designed to be complementary to the neighbouring sites of target DNA. R1 is a pyrene, which takes the place of the heterocyclic base of the 5'-terminal adenosine nucleotide residue in the 5'-AATTCG nucleotide sequence. R2 is a dimethylaminoaniline group substituting for the heterocyclic base of the 3'-terminal cytidine residue in the 5'-GCATGC nucleotide sequence.

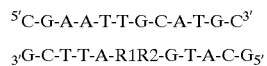

The pyrene group (R1) and the dimethylaminoaniline group (R2) are located in the position of the missed nucleotide residues dA and dC, respectively. The energy minimized structure of above system is presented in FIG. 8.

Figure 9:
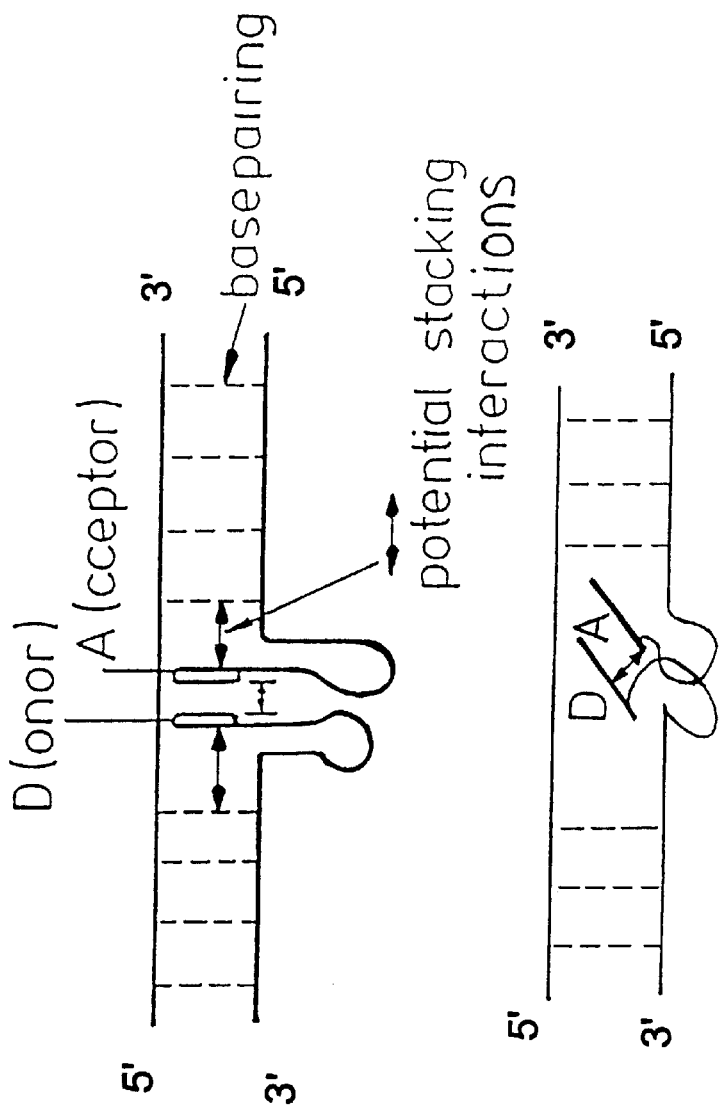

Reference is now made to FIGS. 9–11 which schematically illustrates various ways in which the exciplex partners may be located within the double stranded nucleic acid structure.

As shown in FIG. 9(a), the two partners (donor and acceptor) that form the exciplex are attached to oligonucleotide probes which bind in continuous alignment to a target strand. The exciplex partners are attached to their respective oligonucleotides in such a way as to form a stacking arrangement on top of each other and the bases at the inner most ends of their respective oligonucleotide probes, the donor and acceptor partner stacking approximately parallel to the duplex base pairs. In FIG. 9(b), the bases are on top of one another whilst lying in the major or minor groove or along the surface of the duplex. The arrangements of FIGS. 9(a) and (b) are achieved by perfect complementarity between target (and allowing for the induced distortion of the duplex at the interface of the oligonucleotide probes) and the binary pair of oligonucleotides or by the use of a single-based or double-based gap between the adjacent 3' and 5' of the oligonucleotide probes as shown in FIG. 10(a) (single-based gap) or FIG. 10(b) (double-based gap).

The advantages of these arrangements are:

The exciplex partners are held close to each other and in a mutually hydrophobic, low polarity environment favoring exciplex emission The system is rigidly defined and is an example of an intramolecular system which favours exciplex emission in an extended range of solvent polarities It is possible to incorporate into the exciplex partners atoms, functionalities or components which provide hydrogen bond donors and/or hydrogen bond acceptors and thus achieve added recognition and complex stability by hydrogen bonding to the base pairs of the target strand, especially in those cases wherein a gap of 1, 2 or even more base pairs has been incorporated.

The arrangement can be achieved by stacking interactions such are as used in native B-DNA or by enforcing the exciplex partners to lie alongside each other in the minor or major grooves.

The heterocyclic base unit of the innermost nucleotide units of the oligonucleotide probes of the binary system can be replaced by suitable, chemically modified analogues and which are in fact the exciplex partners.

In this case where there is a gap of one or more nucleotides, detection is achieved by using a series of overlapping oligonucleotides to cover the modified region. In this respect see FIG. 11 in which i=1 for a 1 base gap, 2 for a 2 base gap etc. For full analysis of the target strand a series of experiments would be conducted with shifted location of ON1' and ON2' on the target nucleic acid.

Reference is now made to FIG. 12 which illustrates a development of the invention in which three probes 10–12 are hybridized to a nucleic acid strand 13. In the complex of FIG. 3, there are four complex precursor components, namely A and B which is as described for FIG. 1 and C and D which are also capable of exciplex formation. The arrangement is such that the electromagnetic radiation resulting from dissociation of the exciplex formed from A and B is capable, by fluorescence resonance energy transfer, of photoexciting precursor component C resulting in formation of an exciplex from C and D which is detectable at a different wavelength from the AB exciplex.

What is claimed is:

1. A method of analysing a sample to determine the presence or otherwise therein of a target polynucleotide sequence, the method comprising
   (a) treating the sample under hybridizing conditions with
      (i) a first polynucleotide probe having a 5'-terminal nucleotide labelled with a first chromophoric moiety able on photo-irradiation to form a complex with a second chromophoric moiety, and
      (ii) a second polynucleotide probe labelled at its 3'-terminal nucleotide with moiety, said first and second probes being adapted to bind to mutually exclusive regions of said target sequence such that said moieties are at the proximal ends of the probes and are able to form said complex which is detectably different from the first and second moieties,
   (b) effecting photo-irradiation to cause complex formation, and
   (c) detecting for formation of the complex, characterised in that
   (d) said first and second moieties are different from each other and are capable of forming an exciplex as the detectable complex, and
   (e) the first and second moieties come into exciplex forming relationship in a localised region of greater hydrophobicity than the bulk phase of the sample being analysed.

2. A method as claimed in claim 1 wherein the first and second moieties come into exciplex forming relationship within the immediate vicinity of the double stranded nucleic acid.

3. A method of analysing a sample to determine the presence or otherwise therein of a target polynucleotide sequence, the method comprising
   (a) treating the sample under hybridizing conditions with
      (i) a first polynucleotide probe having a 5'-terminal nucleotide labelled with a first chromophoric moiety able on photo-irradiation to form a complex with a second chromophoric moiety, and
      (ii) a second polynucleotide probe labelled at its 3'-terminal nucleotide with moiety, said first and second probes being adapted to bind to mutually exclusive regions of said target sequence such that said moieties are at the proximal ends of the probes and are able to form said complex which is detectably different from the first and second moieties,
   (b) effecting photo-irradiation to cause complex formation, and
   (c) detecting for formation of the complex, characterised in that
   (d) said first and second moieties are different from each other and are capable of forming an exciplex as the detectable complex, and
   (e) the first and second moieties come into exciplex forming relationship within the immediate vicinity of the double stranded nucleic acid.

4. A method as claimed in claim 2 wherein the exciplex is held in the vicinity of the nucleic acid molecule by weak attractions, hydrogen bonding, Van der Waals forces, dipole-dipole interactions.

5. A method as claimed in any one of claims 2 to 4 wherein the exciplex is formed
   (a) within the duplex structure itself in the manner of surrogate base pair partners with or without actual base pairing;
   (b) lying at least partially within one of the grooves of the double stranded nucleic acid structure; or
   (c) along or across the polyphosphate backbone.

6. A method as claimed in claim 5 wherein the first and second moieties come into exciplex forming relation ship in any of the following ways
   (A) within or within the vicinity of the minor groove of the double stranded nucleic acid;
   (B) within or within the vicinity of the major groove of the double stranded nucleic acid;
   (C) into the region of the axis of the nucleic acid helix;
   (D) between nucleotide base pairs;
   (E) against the polyphosphate anionic and associated (deoxy)ribosyl backbone;
   (F) within a cavity, bulge or distortion formed at or between the adjacent 3' and 5' ends of the oligonucleotide probes.

7. A method as claimed in claim 2 wherein the first or second moiety is bonded to a site selected from the group consisting of the amino groups of guanosine, adenosine or cytidine, the C5 position of cytidine uridine or 2'-deoxyuridine, the N7 position for guanosine or adenosine, and the N3 position of cytidine or adenosine.

8. A method as claimed in claim 1 wherein an additive is incorporated in the sample for providing the localised region of increased hydrophobicity.

9. A method as claimed in claim 8 wherein the additive is a compound capable of acting as a host in a host-guest complex for which the guest is formed of the first and second moieties in exciplex forming relationship.

10. A method as claimed in claim 9 wherein the host is a cyclodextrin cyclophane, calixarene, crown ether, or cryptand.

11. A method as claimed in claimed in claim 10 wherein the additive is a surface active agent, ammonium salt having at least one chain of four or more.

12. A method of analysing a sample to determine the presence or otherwise therein of a target polynucleotide sequence, the method comprising
   (a) treating the sample under hybridizing conditions with
      (i) a first polynucleotide probe having a 5'-terminal nucleotide labelled with a first chromphoric moiety able on photo-irradiation to form a complex with a second chromophoric moiety, and
      (ii) a second polynucleotide probe labelled at its 3'-terminal nucleotide with moiety, said first and second probes being adapted to bind to mutually exclusive regions of said target sequence such that said moieties are at the proximal ends of the probes and are able to form said complex which is detectably different from the first and second moieties,
   (b) effecting photo-irradiation to cause complex formation, and
   (c) detecting for formation of the complex, characterised in that
   (d) said first and second moieties are different from each other and are capable of forming an exciplex as the detectable complex, and
   (e) there is included in the sample being analysed a compound capable of developing an exciplex fluorescent signal when the first and second moieties are in exciplex forming relationship.

13. A method as claimed in claim 12 wherein the additive is a compound capable of acting as a host in a host-guest complex for which the guest is formed of the first and second moieties in exciplex forming relationship.

14. A method as claimed in claim 13 wherein the host is a cyclodextrin, cyclophane, calixarene, crown ether or cryptand.

15. A method as claimed in claimed in claim 12 wherein the additive is a surface active agent.

16. A method as claimed in claim 15 wherein the surface active agent is a quaternary ammonium salt having at least one chain of 4 or more carbon atoms bonded to the quaternary nitrogen atom.

17. A method as claimed in claim 12 wherein the additive comprises a polyanion.

18. A method as claimed in claim 16 wherein the additive is a polysulphate poly(vinyl sulfate), chondroitin sulfate A, B or C, heparin, a polyphosphate, a nucleic acid or semisynthetic nucleic acid (including PNA's and peptide nucleic acids), a polycarboxylate, or a polyanionic polymer containing at least two of carboxylate, phosphate.

19. A method of analysing a sample to determine the presence or otherwise therein of a target polynucleotide sequence, the method comprising
   (a) treating the sample under hybridizing conditions with
      (i) a first polynucleotide probe having a 5'-terminal nucleotide labelled with a first chromphoric moiety able on photo-irradiation to form a complex with a second chromophoric moiety, and
      (ii) a second polynucleotide probe labelled at its 3'-terminal nucleotide with moiety, said first and second probes being adapted to bind to mutually exclusive regions of said target sequence such that said moieties are at the proximal ends of the probes and are able to form said complex which is detectably different from the first and second moieties,
   (b) effecting photo-irradiation to cause complex formation, and
   (c) detecting for formation of the complex, characterised in that
   (d) said first and second moieties are different from each other and are capable of forming an exciplex as the detectable complex, and
   (e) a magnetic field is applied to enhance exciplex emission.

20. A method of analysing a sample to determine the presence or otherwise therein of a target polynucleotide sequence, the method comprising
   (a) treating the sample under hybridizing conditions with
      (i) a first polynucleotide probe having a 5'-terminal nucleotide labelled with a first chromphoric moiety able on photo-irradiation to form a complex with a second chromophoric moiety, and
      (ii) a second polynucleotide probe labelled at its 3'-terminal nucleotide with moiety, said first and second probes being adapted to bind to mutually exclusive regions of said target sequence such that said moieties are at the proximal ends of the probes and are able to form said complex which is detectably different from the first and second moieties,
   (b) effecting photo-irradiation to cause complex formation, and
   (c) detecting for formation of the complex, characterised in that
   (d) said first and second moieties are different from each other and are capable of forming an exciplex as the detectable complex, and in that
   (e) the method involves at least on of the steps, in either order, of (i) at least partial removal of the relatively polar medium, and (ii) addition of a less polar medium thereby to enhance exciplex emission.

21. A method as claimed in any one of claims 1, 3 and 12 wherein the first and second moieties are within 1 nm of each other when in exciplex-forming relationship.

22. A method as claimed in any one of claims 1, 3 and 12 wherein the oligonucleotide probes are adapted to bind to the nucleic acid strand with their adjacent 3' and 5' ends spaced by at least one base of the nucleic acid strand.

23. A method as claimed in claim 22 wherein the adjacent 3' and 5' ends of the oligonucleotide probes are spaced by at most 3 bases of the nucleic acid stands.

24. A method as claimed in any one of claims 1, 3 and 12 wherein the oligonucleotide probes each comprise at least 6 bases.

25. A method as claimed in claim 24 wherein the oligonucleotide probes comprise at least 9 bases.

26. A method as claimed in any one of claims 1, 3 and 12 wherein detection is by time resolved fluorescence.

27. A method as claimed in any one of claims 1, 3 and 12 wherein detection is by circular dichroism.

28. A method as claimed in any one of claims 1, 3 and 12 wherein the nucleic acid is selected from the group consisting of DNA, RNA, a mixed RNA:DNA hybrid and a PNA.

29. A method as claimed in claim 28 wherein the nucleic acid is in combination with other molecules.

30. A method as claimed in claim 28 wherein the nucleic acid is in a chromosome, chromotin or higher cellular structure.

31. A method as claimed in any one of claims 1, 3 and 12 wherein the nucleic acid is single stranded.

32. A method as claimed in any one of claims 1, 3 and 12 wherein the sample is an aqueous sample.

33. The method as claimed in claim 19 or 20 wherein the first and second moieties are within 1 mm of each other when in exciplex-forming relationship.

34. The method as claimed in claim 19 or 20 wherein the oligonucleotide probes are adapted to bind to the nucleic acid strand with their adjacent 3' and 5' ends spaced by at least one base of the nucleic acid strand.

35. The method as claimed in claim 34 wherein the adjacent 3' and 5' ends of oligonucleotide probes are spaced by at most 3 bases of the nucleic acid strands.

36. The method as claimed in claim 19 or 20 wherein the oligonucleotide probes each comprise at least 6 bases.

37. The method as claimed in claim 36 wherein the oligonucleotide probes comprise at least 9 bases.

38. The method as claimed in claim 19 or 20 wherein detection is by time resolved fluorescence.

39. The method as claimed in claim 19 or 20 wherein detection is by circular dichroism.

40. The method as claimed in claim 19 or 20 wherein the nucleic acid is selected from the group consisting of DNA, RNA, a mixed RNA:DNA hybrid and a PNA.

41. The method as claimed in claim 28 wherein the nucleic acid is in combination with other molecules.

42. The method as claimed in claim 28 wherein the nucleic acid is in a chromosome, chromotin or higher cellular structure.

43. The method as claimed in claim 19 or 20 wherein the nucleic acid is single stranded.

44. The method as claimed in claim 19 or 20 wherein the sample is an aqueous sample.

45. The method as claimed in claim 4 wherein said weak attractions are selected from the group consisting of electrostatic forces, hydrogen bonding, Van der Waals forces, dipole-dipole interactions and hydrophobic interactions.

46. The method as claimed in claim 11 wherein the surface active agent is a quaternary ammonium salt having at least one chain of at least four carbon atoms.

47. The method as claimed in claim 18 wherein the polysulfate is selected from the group consisting of poly (vinyl sulfate), chondroitin sulfate A, B or C, heparin, a polyphosphate, a nucleic acid or semi-synthetic nucleic acid, a polycarboxylate, and a polyanionic polymer containing at least two of carboxylate, phosphate and sulfate groups.

\* \* \* \* \*